United States Patent
Evans

(10) Patent No.: US 7,649,000 B2
(45) Date of Patent: Jan. 19, 2010

(54) SELECTIVE DIPEPTIDE INHIBITORS OF KALLIKREIN

(75) Inventor: David Michael Evans, Southampton (GB)

(73) Assignee: Vantia Limited (GB)

(*) Notice: Subject to any disclaimer, the term of this patent is extended or adjusted under 35 U.S.C. 154(b) by 585 days.

(21) Appl. No.: 10/506,535

(22) PCT Filed: Mar. 4, 2003

(86) PCT No.: PCT/GB03/00908

§ 371 (c)(1), (2), (4) Date: Jul. 5, 2005

(87) PCT Pub. No.: WO03/076458

PCT Pub. Date: Sep. 18, 2003

(65) Prior Publication Data

US 2006/0052313 A1     Mar. 9, 2006

(30) Foreign Application Priority Data

Mar. 8, 2002 (GB) .................... 0205527.5

(51) Int. Cl.
*A61K 31/4468* (2006.01)
*C07D 211/56* (2006.01)

(52) U.S. Cl. ............ 514/319; 514/329; 546/205; 546/224

(58) Field of Classification Search ......... 514/319, 514/331, 329; 546/205, 231, 224
See application file for complete search history.

(56) References Cited

FOREIGN PATENT DOCUMENTS

WO   WO9308211    * 4/1993
WO   WO 95/07291    3/1995

OTHER PUBLICATIONS

Griesbacher et al. "Involvement of tissue . . . " Bri. J. Pharm. 137, p. 692-700 (2002).*
McIver et al. "Preparation of tripeptide . . . " Ca 119:226431 (1993).*
Evans "Preparation of acylamino . . . " Ca 139:246221 (2003).*
Baumann et al. "Effect of emotional stress . . . " Ca 95:130620 (1981).*
Gupta "Role of kallikrein . . . " Ca 96:102017 (1982).*
Campbell "Towards understanding the kallikrein . . . " Ca 133:217738 (2000).*
Garrett et al. "Peptide aldehyde . . . " J. peptide Res. 52, p. 62-71 (1998).*
Peake et al. peptide inhibitors . . . Clin. exp. immunol. 79, p. 454-458 (1990).*
Colman "Is the plasma kallikrein . . . " Blood v.108(1) p. 1-2 (2006).*
International Search Report.
T. Griesbacher et al., "Involvement of tissue kallikrein but not plasma kallikrein in the development of symptoms mediated by endogenous kinins in acute pancreatitis in rats", British Journal of Pharmacology, vol. 137, No. 5, Nov. 2002, pp. 692-700, XP002252617, Basingstoke, Hants., GB ISSN: 0007-1188 the whole document.
W.C. Wolf et al., "A synthetic tissue kallikrein inhibitor suppresses cancer cell invasiveness", American Journal of Pathology, vol. 159, No. 5, Nov. 2001, pp. 1797-1805, XP002252618, Philadelphia PA, US, ISSN: 0002-9440 the whole document.
K.D. Bhoola et al., "Bioregulation of Kinins: Kallikreins, Kininogens, and Kininases", Pharmacological Reviews, vol. 44, No. 1, 1992, pp. 1-80.
D. Michael Evans et al., "Selective Inhibitors of Plasma Kallikrein", Immunopharmacology, 32 (1996) pp. 115-116.
D. Michael Evans et al., "Synthetic Inhibitors of Human Tissue Kallikrein", Immunopharmacology, 32 (1996), pp. 117-118.
J. Stürzebecher et al., "Novel Plasma Kallikrein Inhibitors of the Benzamidine Type", Brazilian J Med Biol Res (1994) 27, pp. 1929-1934.
Naoki Teno et al., "Development of Active Center-Directed Plasmin and Plasma Kallikrein Inhibitors and Studies on the Structure-Inhibitory Activity Relationship", Chem. Pharma. Bull. 41(6) pp. 1079-1090 (1993).

(Continued)

*Primary Examiner*—Celia Chang
(74) *Attorney, Agent, or Firm*—Woodcock Washburn LLP

(57) ABSTRACT

Compounds of general formula 1, or a pharmaceutically acceptable salt thereof,

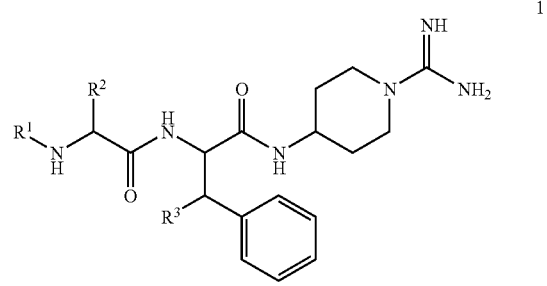

wherein
$R^1$ is selected from H, lower alkyl, $R^4$—CO, $R^4$—$O_2CCH_2$, $R^5$—OCO and $R^5$—$SO_2$;
$R^2$ is selected from lower alkyl, cycloalkyl optionally substituted with an alkyl or alkyloxy group, ($C_5$-$C_{12}$)cycloalkylalkyl optionally substituted with an alkyl or alkyloxy group, aralkyl optionally substituted with up to three groups chosen from F, Cl, Br, I, OH, lower alkyl, O-(lower alkyl), O-benzyl, $NH_2$, $NO_2$, NH-acyl, CN and $CF_3$, and aralkyloxymethyl optionally substituted with up to three groups chosen from F, Cl, Br, OH, lower alkyl and O-(lower alkyl); or
$R^1$ and $R^2$ together are an o-xylylene group optionally substituted on the aromatic ring with a group selected from F, Cl, Br, OH, lower alkyl and O-(lower alkyl);
$R^3$ is selected from H, OH and O-lower alkyl;
$R^4$ is selected from H, lower alkyl and phenyl; and
$R^5$ is selected from lower alkyl, phenyl and benzyl.

The compounds are useful as pharmaceutical compositions.

6 Claims, No Drawings

OTHER PUBLICATIONS

Y. Fujimori et al., "Effects of a Highly Selective Plasma Kallikrein Inhibitor on Collagen-Induced Arthritis in Mice", Agents Actions, 39, (1993), pp. 42-48.

S. Okamoto et al., "A Finding of Highly Selective Synthetic Inhibitor of Plasma Kallikrein: It's Action to Bradykinin Generation, Intrinsic Coagulation and Experimental DIC", Recent Progress on Kinins, 1992, pp. 198-204.

Antoni Stadnicki MD et al., "Selective Plasma Kallikrein Inhibitor Attenuates Acute Intestinal Inflammation in Lewis Rat", Digestive Diseases and Sciences, vol. 41, No. 5, May 1996, pp. 912-920.

J. Sueras-Diaz et al., "Cleavage of human Kininogen fragments at Met-Kys by human tissue kallikrein", Brazilian J Med Biol Res (1994) 27: 1935-1942.

H.T. Johansen et al., "Assay of Kallikrein Inhibitors and Leves of Acetone-Activated Kallikrein in Plasma Specimens from Reactors to Dextran or to Contrast Media", Int. J. Tiss. Reac. VIII(3), pp. 185-192, (1986).

Deepak K. Shori et al., "New Specific Assays for Tonin and Tissue Kallikrein Activities in Rat Submandibular Glands", Biochemical Pharmacology, vol. 43, No. 6, pp. 1209-1217, 1992.

Jörg Stürzebecher et al., "Inhibition of Human Mast Cell Tryptase by Benzamidine Derivatives", Biol. Chem. Hoppe-Seyler, vol. 373, pp. 1025-1030, Oct. 1992.

M. Dixon, "The Determination of Enzyme Inhibitor Constants", Biochemical Laboratory, University of Cambridge, vol. 55, pp. 170-171, 1953.

\* cited by examiner

US 7,649,000 B2

SELECTIVE DIPEPTIDE INHIBITORS OF KALLIKREIN

CROSS-REFERENCE TO RELATED APPLICATIONS

The present application is a U.S. National Stage entry under 35 U.S.C. § 371 of PCT/GB03/00908 filed Mar. 4, 2003, which in turn claims priority under 35 U.S.C § 365 of GB 0205527.5,filed Mar. 8, 2002.

The present invention relates to a series of novel compounds that are selective inhibitors of the enzyme plasma kallikrein, to pharmaceutical compositions comprising these inhibitors, and the use of such compositions in the treatment of human diseases.

BACKGROUND

The enzyme plasma kallikrein, also known by the classification EC.3.4.21.34, is a member of a family of trypsin-like serine protease that also includes tissue kallikrein, thrombin, trypsin and plasmin. It is found in plasma as an inactive zymogen that is activated by Factor XIIa. The enzyme has a broad spectrum of activity. Plasma kallikrein liberates the vasoactive peptide bradykinin from high molecular weight kininogen by cleavage of Lys-Arg and Arg-Ser bonds. The same peptide can also be liberated from low molecular weight kininogen in the presence of neutrophil elastase. It is also capable of activating prourokinase and plasminogen, and is also thought to participate in the conversion of prorenin to renin. Plasma kallikrein is an essential component of the intrinsic blood coagulation cascade although its role does not involve the release of bradykinin or enzymatic cleavage. High molecular weight kininogen, the preferred substrate for plasma kallikrein, is essential for the activation in this cascade (K. D. Bhoola et al., Pharm. Rev., 1992, 44, 1-80).

The physiological effects of plasma kallikrein are likely to result from the proteolytic cleavage of kininogens to liberate kinins or of other substrates, e.g. precursors of growth factors. Kinins such as bradykinin are potent mediators of inflammation. In addition they influence cellular functions such as blood pressure, local blood flow, glucose transport and cell proliferation. These cellular actions which are modified by release of secondary messengers such as platelet activating factor, leukotrienes, prostaglandins, Substance P, acetylcholine and noradrenaline.

Several groups have disclosed synthetic inhibitors of plasma kallikrein. These include arginine ketomethylene derivatives (WO 92/04371 and D. M. Evans et al., Immunopharmacology, 1996, 32, 115-116), noragmatine and agmatine derivatives (WO 95/07291, WO 94/29335), benzamidine derivatives (J. Stürzbecher et al., Brazilian J. Med. Biol. Res. 1994, 27, 1929-1934), boronic acid derivatives (U.S. Pat. No. 5,187,157) and aminomethylcyclohexanoyl derivatives (N. Teno et al., Chem. Pharm. Bull., 1993, 41, 1079-1090). The aminomethylcyclohexanoyl derivatives have been shown to be active in models of collagen-induced arthritis in mice (Y. Fujimora et al., Agents Actions, 1993, 39, 42-48) and endotoxin-induced disseminated intravascular coagulation (DIC) in rats (S. Okamoto et al., Agents Actions (Supplement), 1992, 38 (Part 1), 198-205). The boronic acid derivatives are active in models of inflammatory bowel disease (A. Stadnicki et al., Digestive Diseases and Sciences, 1996, 41, 912-920 and FASEB, 1998, 12,325-333).

Selectivity with respect to the other members of the trypsin-like serine protease family is an important issue. Inhibitors of tissue kallikrein displaying poor plasma kallikrein activity have previously been reported (M. Szelke et al., Brazilian J. Med. Biol. Res. 1994, 27, 1935 and D. M. Evans et al., Immunopharmacology, 1996, 32, 117), but there remains a need for compounds that selectively inhibit plasma kallikrein and not tissue kallikrein.

BRIEF DESCRIPTION OF THE INVENTION

The present invention relates to a series of acylaminopiperidine-1-carboxamidines that are inhibitors of plasma kallikrein. These compounds demonstrate good selectivity for plasma kallikrein, and are potentially useful in the treatment of inflammatory bowel disease, arthritis, inflammation, septic shock, hypotension, cancer, adult respiratory distress syndrome, disseminated intravascular coagulation, cardiopulmonary bypass surgery and bleeding from post-operative surgery. The invention further relates to pharmaceutical compositions of the inhibitors, to the use of the compositions as therapeutic agents, and to methods of treatment using the compositions.

DETAILED DESCRIPTION OF THE INVENTION

In a first aspect, the present invention comprises a series of novel 4-(dipeptidylamino)-piperidine-1-carboxamidines according to general formula 1.

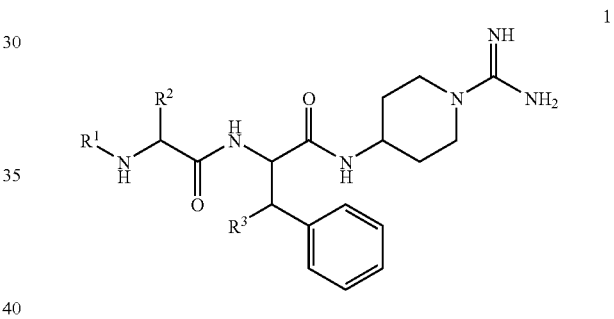

In general formula 1, $R^1$ represents a group selected from a hydrogen atom (H), a lower alkyl group, a group according to $R^4$—CO, a group according to $R^4$—$O_2CCH_2$, a group according to $R^5$—OCO, and a group according to $R^5$—$SO_2$. $R^2$ represents a group selected from a lower alkyl group, a cycloalkyl or ($C_5$-$C_{12}$)cycloalkylalkyl group, either of which may optionally be substituted with an alkyl or alkoxy group, an aralkyl group which may optionally be substituted with up to three groups chosen from F, Cl, Br, I, OH, lower alkyl, O-(lower alkyl), O-benzyl, $NH_2$, $NO_2$, NH-acyl, CN and $CF_3$, and an aralkyloxymethyl group which may optionally be substituted with up to three groups chosen from F, Cl, Br, OH, lower alkyl and O-(lower alkyl). Alternatively, $R^1$ and $R^2$ together may constitute an ortho-xylylene group (o-$C_6H_4$($CH_2)_2$). The aromatic ring of this xylylene group may optionally be substituted with a group selected from F, Cl, Br, OH, lower alkyl and O-(lower alkyl).

$R^3$ represents a group selected from H, OH and O-(lower alkyl).

$R^4$ represents a group selected from H, lower alkyl and phenyl.

$R^5$ represents a group selected from lower alkyl, phenyl and benzyl.

In the context of the present disclosure, the terms "alkyl group" and "lower alkyl group" are used interchangeably to denote linear and branched saturated hydrocarbon groups with between 1 and 8 carbon atoms, such as methyl, ethyl, isopropyl, tert-butyl, neopentyl and isooctyl groups.

The term "cycloalkyl group" is used to denote monocyclic or polycyclic saturated hydrocarbon groups with between 3 and 12 carbon atoms, such as cyclopropyl, cyclohexyl, bicyclo[4.4.0]decyl (i.e. decahydronaphthyl) and adamantyl groups.

The term "cycloakylalkyl group" is used to denote alkyl groups that bear a cycloalkyl group as a substituent, such as cyclohexylmethyl and 1-(cyclopentyl)ethyl groups. Where a limit is specified, as in ($C_a$—$C_b$)cycloalkylalkyl, this denotes that the cycloalkyl moiety has between a and b carbon atoms.

The term "alkoxy group" is used to denote O-(alkyl) groups.

The term "acyl group" is used to denote formyl (H—CO) and alkyl-CO groups.

The term "aralkyl group" is used to denote alkyl groups that bear an aryl group as a substituent, such as benzyl and 1-naphthylmethyl groups. The term "aryl group" includes phenyl, naphthyl, furyl, thienyl, pyrrolyl and pyridyl groups.

The term "aralkyloxymethyl group" is used to denote aralkyl-OCH$_2$ groups.

The compounds of the present invention all have a guanidine functional group and so can form addition salts with acids. To the extent that such acids are pharmaceutically acceptable then these salts fall within the scope of the invention. Examples of suitable acids include acetic acid, trifluoroacetic acid, fumaric acid, malic acid, citric acid, benzoic acid, benzenesulphonic acid, hydrochloric acid, sulphuric acid and phosphoric acid. Certain compounds within the invention have an acidic functional group and so can form salts with alkaline and alkaline earth metals. Again, insofar as these are pharmaceutically acceptable they are included in the scope of the invention. Examples of such salts include the sodium, potassium and calcium salts.

The compounds of the present invention all have at least two stereogenic centres (asymmetric carbon atoms) and so can exist as optical isomers, such as enantiomers, diastereomers and epimers. All such isomers are included in the scope of the present invention. Mixtures of such isomers, including (but not limited to) racemic mixtures are also included in the scope of the invention.

In a preferred embodiment, the present invention comprises compounds according to general formula 1 in which $R^1$ is selected from H, lower alkyl and $R^4$—$O_2CCH_2$.

In another preferred embodiment, the present invention comprises compounds according to general formula 1 in which $R^2$ is selected from ($C_6$-$C_{10}$)cycloalkylalkyl, benzyl optionally substituted with up to three groups chosen from F, Cl, Br, OH, lower alkyl and O-(lower alkyl), phenethyl optionally substituted with up to three groups chosen from F, Cl, Br, OH, lower alkyl and O-(lower alkyl), and benzyloxymethyl optionally substituted with up to three groups chosen from F, Cl, Br, OH, lower alkyl and O-(lower alkyl). More preferably $R^2$ is selected from cyclohexylmethyl, decahydronaphth-2-ylmethyl, benzyl, 4-fluorobenzyl, 4-chlorobenzyl, 4-hydroxybenzyl, 4-(lower alkyl)oxybenzyl, α-hydroxybenzyl, α-methoxybenzyl, phenethyl and benzyloxymethyl.

In another preferred embodiment, the present invention comprises compounds according to general formula 1 in which the absolute stereochemistry is as depicted in general formula 1A. More preferably, the absolute stereochemistry is as depicted in general formula 1B.

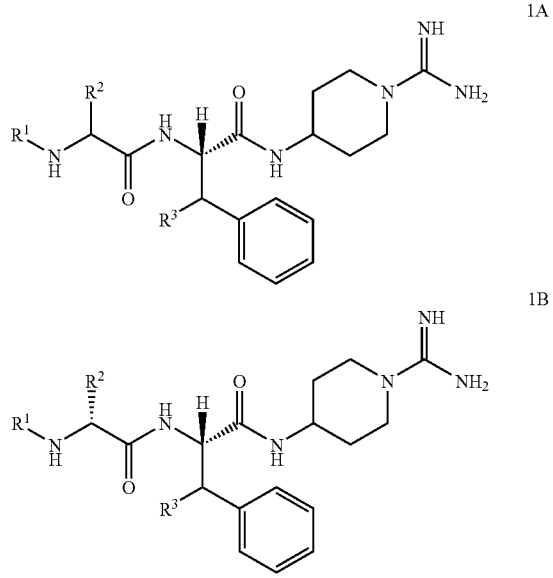

In another preferred embodiment, the present invention comprises a compound selected from:

(2'S,2"R)-4-(2'-(2"-amino-3"-(4'"-ethoxyphenyl)propanoylamino)-3'-phenylpropanoyl-amino)piperidine-1-carboxamidine;

(2'S,2"R)-4-(2'-(2"-carboxymethylamino-3"-(4'"-ethoxyphenyl)propanoylamino)-3'-phenylpropanoylamino)piperidine-1-carboxamidine;

(2'S,2"R)-4-(2'-(3"-(4'"-ethoxyphenyl)-2"-(methyloxycarbonylmethylamino)-propanoylamino)-3'-phenylpropanoylamino)piperidine-1-carboxamidine;

(2-S,2"R)-4-(2'-(2"-amino-3"-cyclohexylpropanoylamino)-3'-phenylpropanoyl-amino)piperidine-1-carboxamidine;

(2'S,2"R)-4-(2'-(2"-carboxymethylamino-3"-cyclohexylpropanoylamino)-3'-phenylpropanoylamino)piperidine-1-carboxamidine;

(2'S,2"R)-4-(2'-(3"-cyclohexyl-2"-(methyloxycarbonylmethylamino)propanoylamino)-3'-phenylpropanoylamino)piperidine-1-carboxamidine;

(2-S,2"R)-4-(2'-(2"-amino-3"-phenylpropanoylamino)-3'-phenylpropanoylamino)piperidine-1-carboxamidine;

(2-S,2"R)-4-(2'-(2"-carboxymethylamino-3"-phenylpropanoylamino)-3'-phenyl-propanoylamino)piperidine-1-carboxamidine;

(2'S,2"R)-4-(2'-(2"-(methyloxycarbonylmethylamino)-3"-phenylpropanoylamino)-3'-phenylpropanoylamino)piperidine-1-carboxamidine;

(2'S,2"R)-4-(2'-(2-amino-3"-decahydronaphth-2'"-ylpropanoylamino)-3'-phenylpropanoyl-amino)piperidine-1-carboxamidine;

(2'S,2"R)-4-(2'-(2"-carboxymethylamino-3"-decahydronaphth-2'"-ylpropanoylamino)-3'-phenylpropanoylamino)piperidine-1-carboxamidine;

(2'S,2"R)-4-(2'-(3"-decahydronaphth-2'"-yl-2"-(methyloxycarbonylmethylamino)propanoyl-amino)-3'-phenylpropanoylamino)piperidine-1-carboxamidine;

(2'S,2"R,3'R)-4-(2'-(2"-amino-3"-cyclohexylpropanoylamino)-3'-hydroxy-3'-phenyl-propanoylamino)piperidine-1-carboxamidine;

(2'S,2"R, 3'R)-4-(2'-(2"-carboxymethylamino-3"-cyclohexylpropanoylamino)-3'-hydroxy-3'-phenylpropanoylamino)piperidine-1-carboxamidine;

(2'S,2"R, 3'R)-4-(2'-(3"-cyclohexyl-2"-(methyloxycarbonylmethylamino)propanoylamino)-3'-hydroxy-3'-phenylpropanoylamino)piperidine-1-carboxamidine;

(2'S,2"R, 3'R)-4-(2'-(2"-amino-3"-(4'"-ethoxyphenyl)propanoylamino)-3'-methoxy-3'-phenyl-propanoylamino)piperidine-1-carboxamidine;

(2'S,2"R,3'R)-4-(2'-(2"-carboxymethylamino-3"-(4'"-ethoxyphenyl)propanoylamino)-3'-methoxy-3'-phenylpropanoylamino)piperidine-1-carboxamidine; and (2'S,2"R, 3'R)-4-(2'-(3"-(4'"-ethoxyphenyl)-2"-(methyloxycarbonylmethylamino)-propanoylamino)-3'-methoxy-3'-phenylpropanoylamino)piperidine-1-carboxamidine.

The compounds of the present invention may be prepared by the methods generally known in the art, and particularly those methods used in the field of peptide chemistry. A useful starting material is 4-amino-1-benzylpiperidine (2). Protection of the primary amine with a tert-butyloxycarbonyl (Boc) group to give 3 and hydrogenolysis provides piperidine derivative 4. This can be treated with isothiourea derivative 5 to give the carboxamidinopiperidine derivative 6 in which the amine and guanidine functional groups are differentially protected.

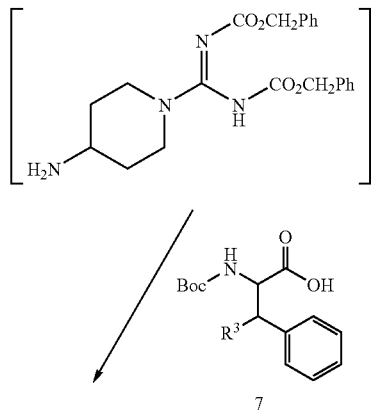

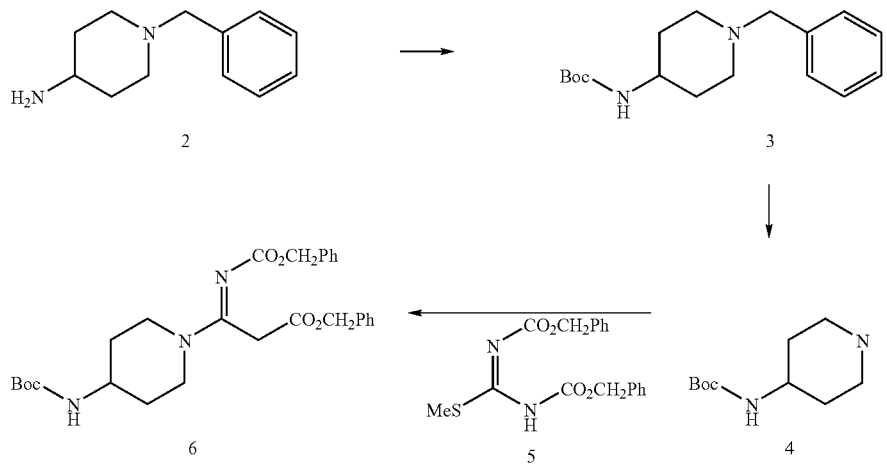

The carboxamidinopiperidine derivative 6 can then be selectively deprotected and coupled to an N-protected amino acid 7 to give intermediate 8.

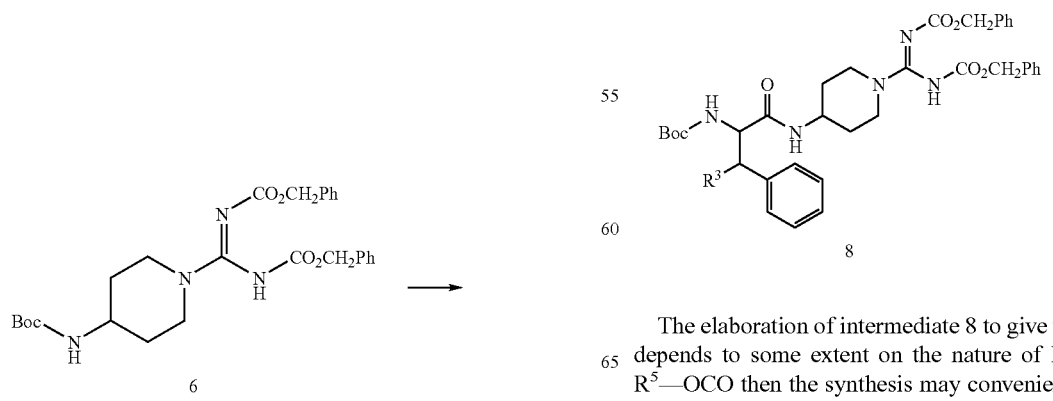

The elaboration of intermediate 8 to give the final product depends to some extent on the nature of $R^1$. When $R^1$ is $R^5$—OCO then the synthesis may conveniently proceed via intermediate 9.

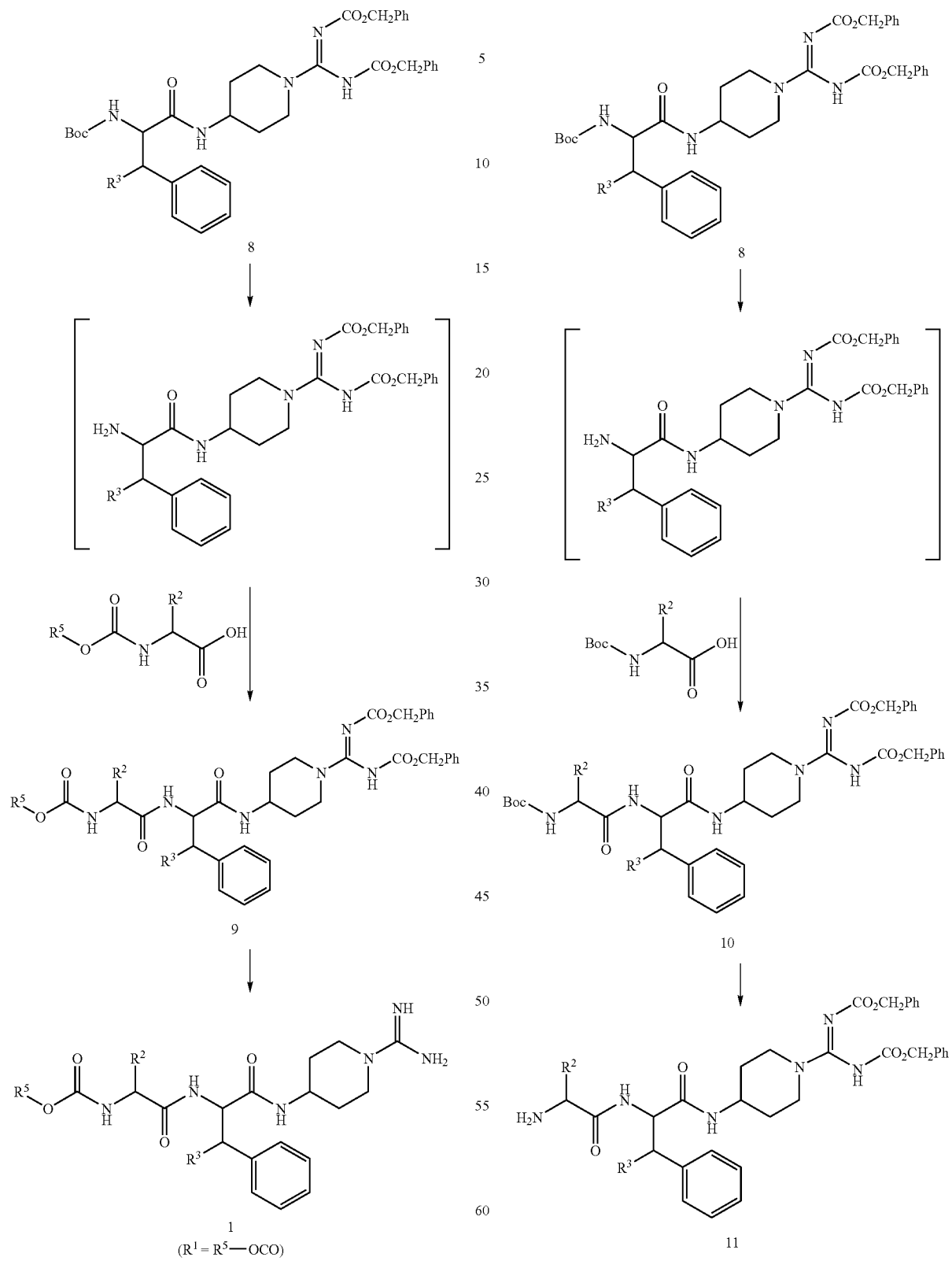
When $R^1$ is H, $R^4$—CO, $R^4$—O$_2$CCH$_2$ or $R^5$—SO$_2$ then the synthesis may conveniently proceed via intermediates 10 and 11.
Deprotection of the guanidine functional group gives compounds according to general formula 1 in which $R^1$ is H. Derivatisation of the primary amine prior to deprotection of the guanidine gives access to other embodiments of $R^1$.

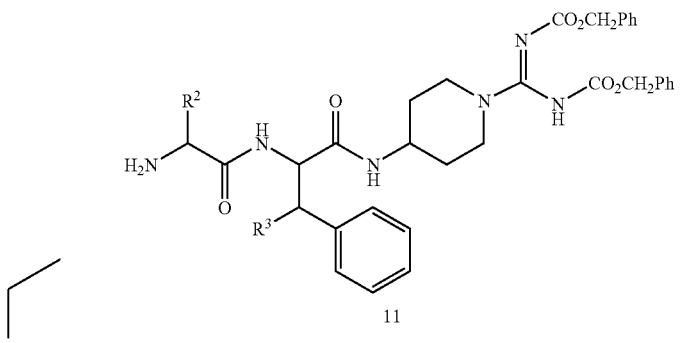
11
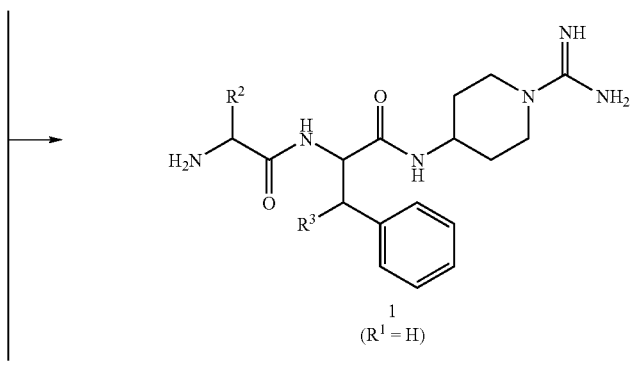
1
(R¹ = H)
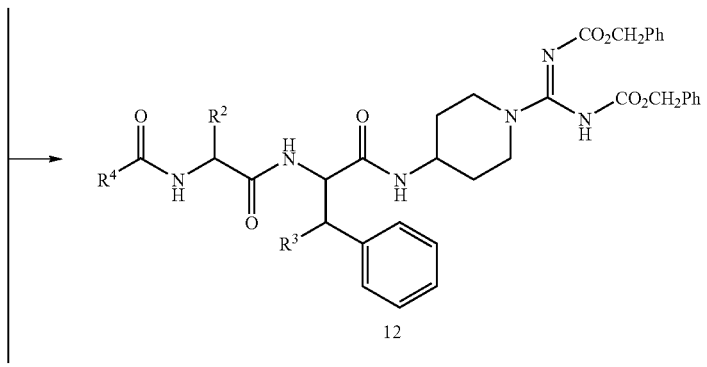
12
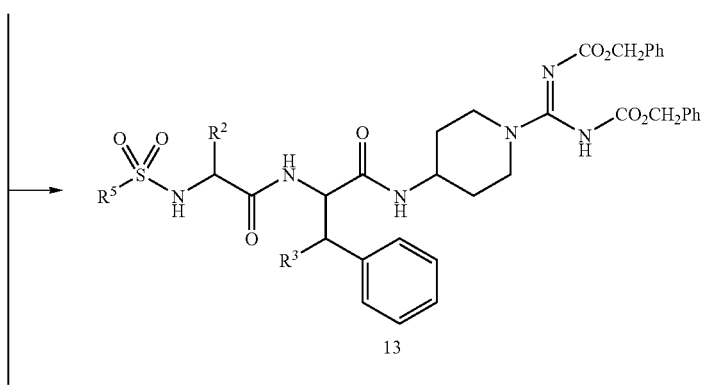
13

-continued

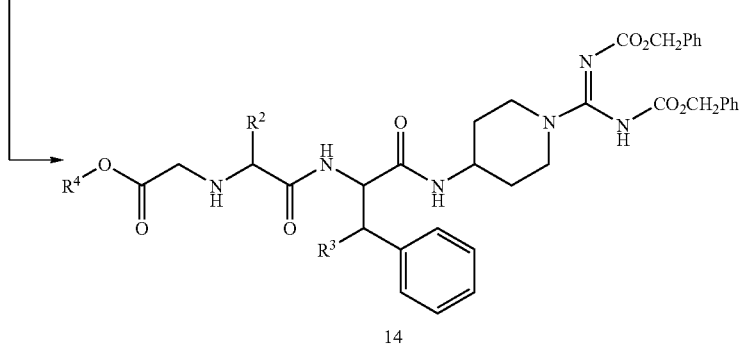

14

Intermediates 12, 13 and 14 may then be deprotected to give the corresponding compounds according to general formula 1.

When $R^1$ is alkyl, or when $R^1$ and $R^2$ together form a xylylene group, the synthesis may conveniently proceed via intermediate 15.

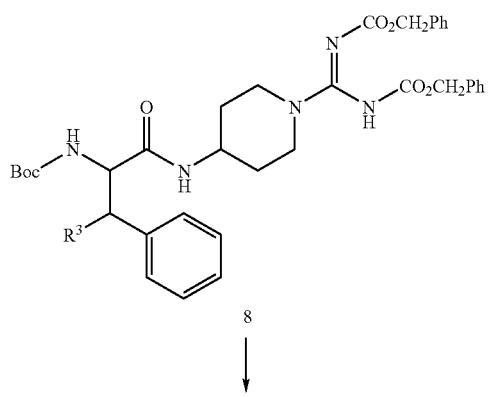

8

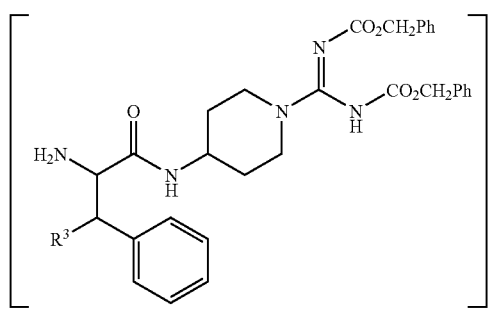

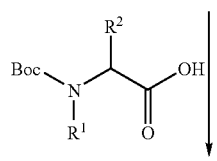

-continued

15

Two deprotection steps then give the corresponding compounds according to general formula 1.

The compounds of the present invention are potent and selective inhibitors of plasma kallikrein. They are therefore useful in the treatment of disease conditions for which over activity of plasma kallikrein is a causative factor. Generally, for use in such treatment the compounds will be formulated for administration to the patient. The pharmaceutical formulation may be a solid or liquid, such as a tablet, capsule, solution or suspension. Methods of preparing such formulations are well known in the pharmaceutical art.

The compositions will be administered to the patient under the supervision of the attending physician.

EXAMPLES

The following abbreviations have been used:
AcOH acetic acid
Boc-DCha-OH N-(tert-butyloxycarbonyl)-3-cyclohexyl-D-alanine
Boc-DTyr(Et)-OH N-(tert-butyloxycarbonyl)-O-ethyl-D-tyrosine
Boc-Phe-ONSu N-(tert-butyloxycarbonyl)-phenylalanine succinimidyl ester
DMF dimethylformamide
H-thPse-OH threo-3-phenylserine
mplc medium pressure liquid chromatography
TFA trifluoroacetic acid
"Celite" is a registered trademark of Celite Corp.
"Vydac" is a registered trademark of W.R. Grace & Co.

Example 1

(2'S,2"R)-4-(2'-(2"-Amino-3"-(4"'-ethoxyphenyl)
propanoylamino)-3'-phenylpropanoyl-amino)piperi-
dine-1-carboxamidine trifluoroacetate

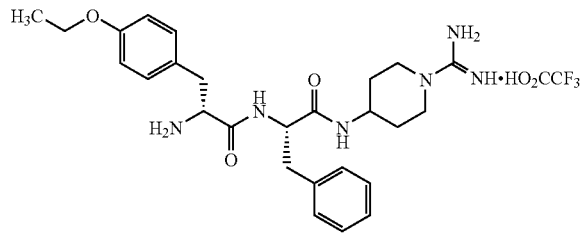

1A.
1-Benzyl-4-(tert-butyloxycarbonylamino)piperidine

4-Amino-1-benzylpiperidine (3.2 g, 16.8 mmol) was dissolved in $CH_2Cl_2$ (100 ml). Di-tert-butyl dicarbonate (3.7 g, 17.0 mmol) and N,N-diisopropylethylamine (1.9 g, 19 mmol) were added. The mixture was stirred for 18 h at room temperature then the solvent was removed in vacuo and the residue was taken up in ethyl acetate (150 ml). This solution was washed with 0.3M $KHSO_4$ (2×30 ml), sat. $NaHCO_3$ (2×30 ml), water (2×30 ml) and brine (1×30 ml), dried ($Na_2SO_4$) and evaporated in vacuo to give a yellow oil which was purified by flash chromatography on silica gel (eluant: 70% chloroform, 30% cyclohexane) to give a yellow solid identified as 1-benzyl-4-(tert-butyloxycarbonylamino)piperidine (4.9 g, 18.9 mmol, 100%).

1B. 4-(tert-Butyloxycarbonylamino)piperidine

1-Benzyl-4-(tert-butyloxycarbonylamino)piperidine (4.9 g, 18.9 mmol) was dissolved in ethanol (100 ml). This solution was hydrogenated over 10% palladium on charcoal at 60 psi. After 18 h at room temperature the mixture was filtered through Celite and the residue washed with ethanol (100 ml). The combined filtrates were evaporated in vacuo to give a white solid identified as 4-(tert-butyloxycarbonylamino)piperidine (2.3 g, 7.1 mmol, 51%).

1C. N,N'-Di(benzyloxycarbonyl)-4-(tert-butyloxy-carbonylamino)piperidine-1-carboxamidine 4-(tert-Butyloxycarbonylamino)piperidine (1.5 g, 7.5 mmol) was dissolved in ethanol (100 ml). N,N'-Bis(benzyloxycarbonyl)-S-methylisothiourea (3.1 g, 8.7 mmol) and mercuric oxide (1.9 g, 8.8 mmol) were added. The mixture was stirred at 40° C. for 4 h then the solid was filtered off and washed with ethanol (50 ml). The combined filtrates were evaporated in vacuo to give a colourless oil which was purified by flash chromatography on silica gel (eluant: 90% pet ether 60-80, 10% ethyl acetate) to give a colourless oil identified as N,N'-di(benzyloxycarbonyl)-4-(tert-butyloxycarbonylamino)piperidine-1-carboxamidine (3.3 g, 6.6 mmol, 87%).

1D. (2'S)-N,N'-Di(benzyloxycarbonyl)-4-(2'-(tert-butyloxycarbonylamino)-3'-phenyl-propanoylamino) piperidine-1-carboxamidine N,N'-Di(benzyloxycarbonyl)-4-(tert-butyloxycarbonylamino)piperidine-1-carboxamidine (3.1 g, 6.1 mmol) was dissolved in 4M HCl/dioxan (70 ml). After 30 min at room temperature the solvent was evaporated in vacuo and the residue was dissolved in $CH_2Cl_2$ (60 ml). This solution was cooled to 0° C., Boc-Phe-ONSu (2.2 g, 6.1 mmol) was added and the pH adjusted to 9 with N-methylmorpholine. The mixture was stirred at room temperature for 4 h, the solvent was evaporated in vacuo and the residue dissolved in ethyl acetate (200 ml). This solution was washed with 0.3M $KHSO_4$ (2×30 ml), sat. $NaHCO_3$ (2×30 ml), water (2×30 ml) and brine (1×30 ml), dried ($Na_2SO_4$) and evaporated in vacuo to give a white solid which was purified by flash chromatography on silica gel (eluant: 70% chloroform, 30% cyclohexane) to give a white solid identified as (2'S)-N,N'-di(benzyloxycarbonyl)-4-(2'-(tert-butyloxycarbonylamino)-3'-phenylpropanoylamino)piperidine-1-carboxamidine (3.56 g, 5.4 mmol, 89%).

1E. (2'S,2"R)-N,N'-Di(benzyloxycarbonyl)-4-(2'-(2"-(tert-butyloxycarbonylamino)-3"-(4"'-ethoxyphenyl) propanoylamino)-3'-phenylpropanoylamino)piperi-dine-1-carboxamidine (2'S)-N,N'-Di(benzyloxycarbonyl)-4-(2'-(tert-butyloxycarbonylamino)-3'-phenylpropanoyl-amino)piperidine-1-carboxamidine (2.5 g, 3.85 mmol) was dissolved in 4M HCl/dioxan (70 ml). After 30 min at room temperature the solvent was evaporated in vacuo and the residue dissolved in $CH_2Cl_2$/DMF (9:1, 50 ml). This solution was cooled to 0° C. and Boc-DTyr(Et)-OH (1.2 g, 3.84 mmol) was added followed by 1-hydroxybenzotriazole hydrate (680 mg, 5.0 mmol) and water-soluble carbodiimide (1.0 g, 5.0 mmol). After 15 min the pH adjusted to 8 with N-methylmorpholine The mixture was stirred at room temperature for 18 h, after which time the solvent was evaporated in vacuo and the residue dissolved in chloroform (200 ml). This solution was washed with 0.3M $KHSO_4$ (2×30 ml), sat. $NaHCO_3$ (2×30 ml), water (2×30 ml) and brine (1×30 ml), dried ($Na_2SO_4$) and evaporated in vacuo to give a white solid which was purified by flash chromatography on silica gel (eluant: 85% chloroform, 15% hexane) to give a white solid identified as (2'S,2"R)-N,N'-di(benzyloxycarbonyl)-4-(2'-(2"-(tert-butyloxycarbonylamino)-3"-(4"'-ethoxyphenyl)-propanoylamino)-3'-phenylpropanoylamino)piperidine-1-carboxamidine (2.47 g, 3.2 mmol, 65%).

1F. (2'S,2"R)-4-(2'-(2"-Amino-3"-(4"'-ethoxyphenyl) propanoylamino)-3'-phenylpropanoyl-amino)piperi-dine-1-carboxamidine trifluoroacetate (2'S,2"R)-N,N'-Di(benzyloxycarbonyl)-4-(2'-(2"-(tert-butyloxycarbonylamino)-3"-(4"'-ethoxyphenyl)propanoylamino)-3'-phenylpropanoylamino)piperidine-1-carboxamidine (2.1 g, 2.7 mmol) was dissolved in 4M HCl/dioxan (50 ml). After 30 min at room temperature the solvent was evaporated in vacuo and the residue dissolved in AcOH/water (95:5, 50 ml). This solution was hydrogenated over 10% palladium on charcoal. After 2 h at room temperature the mixture was filtered through Celite and the residue washed with AcOH/water (9:1, 30 ml). The combined filtrates were evaporated in vacuo and the residue purified by mplc on Vydac $C_{18}$ (15-25μ) using $MeCN/H_2O$/TFA to give a white solid identified as H-DTyr(Et)-Phe4-amino-1-amidinopiperidine trifluoroacetate (1.12 g).

$[M+H]^+=480.6$

Example 2

(2'S,2"R)-4-(2'-(3"-Cyclohexyl-2"-(methyloxycarbonylmethylamino)propanoylamino)-3'-phenylpropanoylamino)piperidine-1-carboxamidine trifluoroacetate

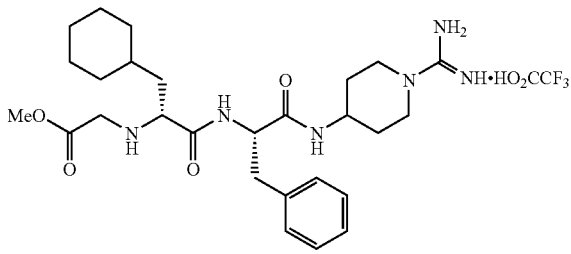

2A. (2'S,2"R)-N,N'-Di(benzyloxycarbonyl)-4-(2'-(2"-(tert-butyloxycarbonylamino)-3"-cyclohexylpropanoylamino)-3'-phenylpropanoylamino)piperidine-1-carboxamidine (2'S)-N,N'-Di(benzyloxycarbonyl)-4-(2'-(tert-butyloxycarbonylamino)-3'-phenylpropanoyl-amino)piperidine-1-carboxamidine (from Example 1D, 1.9 g, 2.99 mmol) was dissolved in 4M HCl/dioxan (70 ml). After 30 min at room temperature the solvent was evaporated in vacuo and the residue dissolved in $CH_2Cl_2$/DMF (9:1, 50 ml). This solution was cooled to 0° C. and Boc-DCha-OH (900 mg, 3.3 mmol) was added followed by 1-hydroxybenzotriazole hydrate (820 mg, 6.1 mmol) and water-soluble carbodiimide (730 mg, 3.6 mmol). After 15 min the pH was adjusted to 8 with N-methylmorpholine. The mixture was stirred at room temperature for 18 h, after which time the solvent was evaporated in vacuo and the residue dissolved in chloroform (200 ml). This solution was washed with 0.3M $KHSO_4$ (2×30 ml), sat. $NaHCO_3$ (2×30 ml), water (2×30 ml) and brine (1×30 ml), dried ($Na_2SO_4$) and evaporated in vacuo to give a white solid which was purified by flash chromatography on silica gel (eluant: 90% chloroform, 10% hexane) to give a white solid identified as (2'S,2"R)-N,N'-di(benzyloxycarbonyl)-4-(2'-(2"-(tert-butyloxycarbonylamino)-3"-cyclohexyl-propanoylamino)-3'-phenylpropanoylamino)piperidine-1-carboxamidine (1.73 g, 2.14 mmol, 72%).

2B. (2'S,2"R)-N,N'-Di(benzyloxycarbonyl)-4-(2'-(3"-cyclohexyl-2"-(methyloxycarbonyl-methylamino)propanoylamino)-3'-phenylpropanoylamino)piperidine-1-carboxamidine (2'S,2"R)-N,N'-Di(benzyloxycarbonyl)-4-(2'-(2"-(tert-butyloxycarbonylamino)-3"-cyclohexyl-propanoylamino)-3'-phenylpropanoylamino)piperidine-1-carboxamidine (1.73 g, 2.14 mmol) was dissolved in 4M HCl/dioxan (50 ml). After 30 min at room temperature the solvent was evaporated in vacuo and the residue dissolved in acetonitrile (100 ml). Methyl bromoacetate (400 mg, 2.6 mmol) and N,N-diisopropylethylamine (440 mg, 4.4 mmol) were added. The reaction mixture was stirred at 60° C. for 5 h after which time the solvent was evaporated in vacuo and the residue dissolved in ethyl acetate (200 ml). This solution was washed with 0.3M $KHSO_4$ (2×30 ml), sat. $NaHCO_3$ (2×30 ml), water (2×30 ml) and brine (1×30 ml), dried ($Na_2SO_4$) and evaporated in vacuo to give a yellow oil which was purified by flash chromatography on silica gel (eluant: 90% chloroform, 10% hexane) to give a white solid identified as (2'S,2"R)-N,N'-di(benzyloxycarbonyl)-4-(2'-(3"-cyclohexyl-2"-(methyloxycarbonylmethylamino)propanoylamino)-3'-phenylpropanoylamino)piperidine-1-carboxamidine (1.65 g, 2.11 mmol, 98%).

2C. (2'S,2"R)-4-(2'-(3"-Cyclohexyl-2"-(methyloxycarbonylmethylamino)propanoylamino)-3'-phenylpropanoylamino)piperidine-1-carboxamidine trifluoroacetate (2-S,2"R)-N,N'-Di(benzyloxycarbonyl)-4-(2'-(3"-cyclohexyl-2"-(methyloxycarbonyl-methylamino)propanoylamino)-3'-phenylpropanoylamino)piperidine-1-carboxamidine (1.62 g, 2.11 mmol) was dissolved in AcOH/water (95:5, 50 ml). This solution was hydrogenated over 10% palladium on charcoal. After 2 h at room temperature the mixture was filtered through Celite and the residue washed with AcOH/water (9:1, 30 ml). The combined filtrates were evaporated in vacuo and the residue purified by mplc on Vydac$C_{18}$ (15-25μ) using MeCN/$H_2O$/TFA to give a white solid identified as (2'S,2"R)-4-(2'-(3"-cyclohexyl-2"-(methyloxycarbonylmethylamino)propanoylamino)-3'-phenylpropanoyl-amino)piperidine-1-carboxamidine trifluoroacetate (570 mg).

$[M+H]^+=515$

Example 3

(2'S,2"R)-4-(2'-(2"-(Carboxymethylamino)-3"-cyclohexylpropanoylamino)-3'-phenyl-propanoylamino)piperidine-1-carboxamidine trifluoroacetate

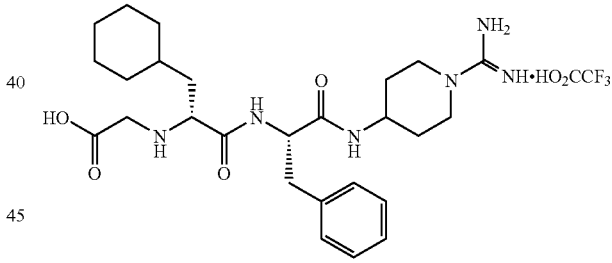

3A. (2-S,2"R)-N,N'-Di(benzyloxycarbonyl)-4-(2'-(2"-(carboxymethylamino)-3"-cyclohexyl-propanoylamino)-3'-phenylpropanoylamino)piperidine-1-carboxamidine (2'S,22"R)-N,N'-Di(benzyloxycarbonyl)-4-(2'-(3"-cyclohexyl-2"-(methyloxycarbonyl-methylamino)propanoylamino)-3'-phenylpropanoylamino)piperidine-1-carboxamidine (from Example 2B, 1.6 g, 2.1 mmol) was dissolved in tetrahydrofuran (50 ml). 1M Lithium hydroxide (3 ml, 3 mmol) was added. After 18 h the solvent was evaporated in vacuo and the residue dissolved in ethyl acetate (150 ml). This solution was washed with 1M citric acid (1×30 ml), water (2×30 ml) and brine (1×30 ml), dried ($Na_2SO_4$) and evaporated in vacuo to give a white solid identified as (2'S,2"R)-N,N'-di(benzyloxycarbonyl)-4-(2'-(2"-(carboxymethylamino)-3"-cyclohexylpropanoylamino)-3'-phenylpropanoylamino)piperidine-1-carboxamidine (1.62 g, 2.11 mmol, 100%).

3B. (2'S,2"R)-4-(2'-(2"-(Carboxymethylamino)-3"-cyclohexylpropanoylamino)-3'-phenyl-propanoylamino)piperidine-1-carboxamidine trifluoroacetate (2'S,2"R)-N,N'-Di(benzyloxycarbonyl)-4-(2'-(2"-(carboxymethylamino)-3"-cyclohexyl-propanoylamino)-3'-phenylpropanoylamino)piperidine-1-carboxamidine (1.62 g, 2.11 mmol) was dissolved in AcOH/water (95:5, 50 ml). This solution was hydrogenated over 10% palladium on charcoal. After 2 h at room temperature the mixture was filtered through Celite and the residue washed with AcOH/water (9:1, 30 ml). The combined filtrates were evaporated in vacuo and the residue purified by mplc on Vydac $C_{18}$ (15-25µ) using MeCN/$H_2$O/TFA to give a white solid identified as (2'S,2"R)-4-(2'-(2"-(carboxymethylamino)-3"-cyclohexylpropanoylamino)-3'-phenylpropanoylamino)piperidine-1-carboxamidine trifluoroacetate (570 mg).
$[M+H]^+=501$

Example 4

(2'S,2"R)-4-(2'-(2"-Benzoylamino-3"-(4"'-ethoxyphenyl)propanoylamino)-3'-phenyl-propanoylamino)piperidine-1-carboxamidine trifluoroacetate

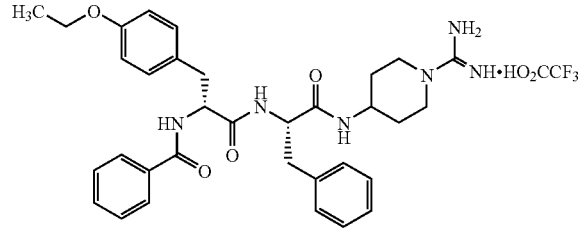

4A. (2'S,2"R)-4-(2'-(2"-Benzoylamino-3"-(4"'-ethoxyphenyl)propanoylamino)-3'-phenyl-propanoylamino)-N,N'-di(benzyloxycarbonyl)piperidine-1-carboxamidine (2'S,2"R)-N,N'-Di(benzyloxycarbonyl)-4-(2'-(2"-(tert-butyloxycarbonylamino)-3"-(4'-ethoxyphenyl)propanoylamino)-3'-phenylpropanoylamino)piperidine-1-carboxamidine (from Example 1F, 100 mg, 0.12 mmol) was dissolved in 4M HCl/dioxan (20 ml). After 30 min at room temperature the solvent was evaporated in vacuo and the residue dissolved in $CH_2Cl_2$ (20 ml). This solution was cooled to 0° C. and benzoyl chloride (19.7 mg, 0.141 mmol) and triethylamine (36 mg, 0.36 mmol) were added. The mixture was stirred at room temperature for 18 h, the solvent was evaporated in vacuo and the residue dissolved in ethyl acetate (70 ml). This solution was washed with 0.3M $KHSO_4$ (2×20 ml), sat. $NaHCO_3$ (2×20 ml), water (2×20 ml) and brine (1×20 ml), dried ($Na_2SO_4$) and evaporated in vacuo to give a white solid which was purified by flash chromatography on silica gel (eluant: 85% chloroform, 15% cyclohexane) to give a white solid identified as (2'S,2"R)-4-(2'-(2"-benzoylamino-3"-(4"'-ethoxyphenyl)propanoylamino)-3'-phenylpropanoylamino)-N,N'-di(benzyloxycarbonyl)piperidine-1-carboxamidine (65 mg, 0.072 mmol, 60%).

4B. (2'S,2"R)-4-(2'-(2"-Benzoylamino-3"-(4"'-ethoxyphenyl)propanoylamino)-3'-phenyl-propanoylamino)piperidine-1-carboxamidine trifluoroacetate (2'S,2"R)-4-(2'-(2"-Benzoylamino-3"-(4"'-ethoxyphenyl)propanoylamino)-3'-phenyl-propanoylamino)-N,N'-di(benzyloxycarbonyl)piperidine-1-carboxamidine (65 mg, 0.072 mmol) was dissolved in AcOH/water (95:5, 25 ml). This solution was hydrogenated over 10% palladium on charcoal. After 1 hour at room temperature the mixture was filtered through Celite and the residue washed with AcOH/water (9:1, 20 ml). The combined filtrates were evaporated in vacuo and the residue purified by mplc on Vydac$C_{18}$ (15-25µ) using MeCN/$H_2$O/TFA to give a white solid identified as (2'S,2"R)-4-(2'-(2"-benzoylamino-3"-(4"'-ethoxyphenyl)propanoylamino)-3'-phenylpropanoylamino)piperidine-1-carboxamidine trifluoroacetate (44 mg).
$[M+H]^+=585$

Example 5

(2'S,2"R, 3'R)-4-(2'-(2"-Amino-3"-(4"'-ethoxyphenyl)propanoylamino)-3'-hydroxy-3'-phenyl-propanoylamino)piperidine-1-carboxamidine trifluoroacetate

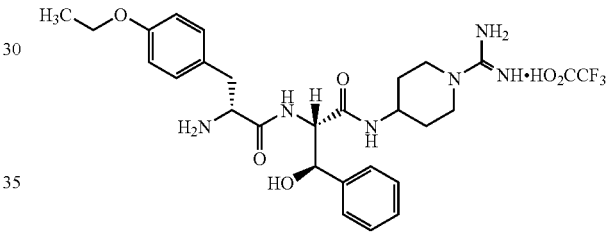

5A. (2S,3R)-2-(tert-Butyloxycarbonylamino)-3-hydroxy-3-phenylpropanoic acid H-thPse-OH (J. Biol. Chem., 1953, 204, 323) (1.4 g, 7.73 mmol) was dissolved in dioxan (75 ml). Sodium hydroxide 820 mg, 20.5 mmol) in water (75 ml) was added followed by di-tert-butyl dicarbonate (2.1 g, 9.6 mmol). The mixture was stirred for 18 h at room temperature then the dioxan was removed in vacuo and the residue was washed with diethyl ether (1×100 ml), acidified to pH 4 with 1M HCl and extracted with $CHCl_3$ (3×100 ml). The combined extracts were washed with water (1×50 ml) and brine (1×50 ml), dried ($Na_2SO_4$) and evaporated in vacuo to give a white solid identified as (2S,3R)-2-(tert-butyloxycarbonylamino)-3-hydroxy-3-phenylpropanoic acid (1.6 g, 5.7 mmol, 74%).

5B (2'S,3'R)-N,N'-Di(benzyloxycarbonyl)-4-(2'-(tert-butyloxycarbonylamino)-3'-hydroxy-3'-phenylpropanoylamino)piperidine-1-carboxamidine N,N'-Di(benzyloxycarbonyl)-4-(tert-butyloxycarbonylamino)piperidine-1-carboxamidine (from Example 1C, 2.3 g, 4.5 mmol) was dissolved in 4M HCl/dioxan (70 ml). After 30 min at room temperature the solvent was evaporated in vacuo and the residue dissolved in $CH_2Cl_2$/DMF (9:1, 50 ml). This solution was cooled to 0° C. and (2S,3R)-2-(tert-butyloxycarbonylamino)-3-hydroxy-3-phenylpropanoic acid (1.6 g, 5.6 mmol) was added followed by 1-hydroxybenzotriazole hydrate (1.1 g, 8.1 mmol) and water-soluble carbodiimide (1.4 g, 75.0 mmol). After 15 min the pH adjusted to 8 with N-methylmorpholine. The mixture was stirred at room temperature for 18 h, after which time the solvent was evaporated in vacuo and the residue dissolved in ethyl acetate (200 ml). This solution was washed with 0.3M $KHSO_4$ (2×30 ml), sat. $NaHCO_3$ (2×30 ml), water (2×30 ml) and brine (1×30 ml), dried ($Na_2SO_4$) and evaporated in vacuo to give a white solid which was purified by flash chromatography on silica gel (eluant: 50% ethyl acetate, 50% pet. ether) to give a white solid identified as (2'S,3'R)-N,N'-di(benzyloxycarbonyl)-4-(2'-(tert-butyloxycarbonylamino)-3'-hydroxy-3'-phenylpropanoylamino)piperidine-1-carboxamidine (1.1 g, 1.6 mmol, 36%).

5C. (2'S,2"R,3'R)-N,N'-Di(benzyloxycarbonyl)-4-(2'-(2"-(tert-butyloxycarbonylamino)-3"-(4'"-ethoxyphenyl)propanoylamino)-3'-hydroxy-3'-phenylpropanoylamino)piperidine-1-carboxamidine (2'S,3'R)-N,N'-Di(benzyloxycarbonyl)-4-(2'-(tert-butyloxycarbonylamino)-3'-hydroxy-3'-phenylpropanoylamino) piperidine-1-carboxamidine (1.1 g, 1.6 mmol) was dissolved in 4M HCl/dioxan (70 ml). After 30 min at room temperature the solvent was evaporated in vacuo and the residue dissolved in $CH_2Cl_2$/DMF (9:1, 50 ml). This solution was cooled to 0° C. and Boc-DTyr(Et)-OH (620 mg, 2.0 mmol) was added followed by 1-hydroxybenzotriazole hydrate (270 mg, 2.0 mmol) and water-soluble carbodiimide (420 mg, 2.1 mmol). After 15 min the pH was adjusted to 8 with N-methylmorpholine The mixture was stirred at room temperature for 18 h, after which time the solvent was evaporated in vacuo and the residue dissolved in ethyl acetate (200 ml). This solution was washed with 0.3M $KHSO_4$ (2×30 ml), sat. $NaHCO_3$ (2×30 ml), water (2×30 ml) and brine (1×30 ml), dried ($Na_2SO_4$) and evaporated in vacuo to give a white solid which was purified by flash chromatography on silica gel (eluant: 60% ethyl acetate, 40% pet. ether) to give a white solid identified as (2'S,2"R,3'R)-N,N'-di(benzyloxycarbonyl)-4-(2'-(2"-(tert-butyloxycarbonylamino)-3"-(4'"-ethoxyphenyl)propanoylamino)-3'-hydroxy-3'-phenylpropanoylamino)piperidine-1-carboxamidine (1.2 g, 1.3 mmol, 80%).

5D. (2'S,2"R,3'R)-4-(2'-(2"-Amino-3"-(4'"-ethoxyphenyl)propanoylamino)-3'-hydroxy-3'-phenylpropanoylamino)piperidine-1-carboxamidine trifluoroacetate (2'S,2"R, 3'R)-N,N'-Di(benzyloxycarbonyl)-4-(2'-(2"-(tert-butyloxycarbonylamino)-3"-(4 W-ethoxyphenyl)propanoylamino)-3'-hydroxy-3'-phenylpropanoylamino)piperidine-1-carboxamidine (1.2 g, 1.3 mmol) was dissolved in 4M HCl/dioxan (50 ml). After 30 min at room temperature the solvent was evaporated in vacuo and the residue dissolved in AcOH/water (95:5, 50 ml). This solution was hydrogenated over 10% palladium on charcoal. After 2 h at room temperature the mixture was filtered through Celite and the residue washed with AcOH/water (9:1, 30 ml). The combined filtrates were evaporated in vacuo and the residue purified by mplc on Vydac $C_{18}$ (15-25μ) using $MeCN/H_2O$/TFA to give a white solid identified as (2'S,2"R,3'R)-4-(2'-(2"-amino-3"-(4'"-ethoxyphenyl)-propanoylamino)-3'-hydroxy-3'-phenylpropanoylamino)piperidine-1-carboxamidine trifluoroacetate (540 mg).

[M+H]$^+$=497.0

Example 6

(2'S,2"R,3'R)-4-(2'-(2"-Amino-3"-(4'"-ethoxyphenyl) propanoylamino)-3'-methoxy-3'-phenyl-propanoylamino)piperidine-1-carboxamidine trifluoroacetate

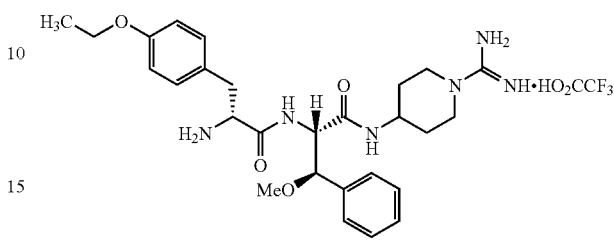

6A. (2'SR,3'RS)-N,N'-Di(benzyloxycarbonyl)-4-(2'-(tert-butyloxycarbonylamino)-3'-hydroxy-3'-phenylpropanoylamino)piperidine-1-carboxamidine (2'SR,3'RS)-N,N'-Di(benzyloxycarbonyl)-4-(2'-(tert-butyloxycarbonylamino)-3'-hydroxy-3'-phenylpropanoylamino)piperidine-1-carboxamidine was prepared by the same method as described in Example 5 but starting with racemic H-thPse-OH.

6B. (2'SR,3'RS)-N,N'-Di(benzyloxycarbonyl)-4-(2'-(tert-butyloxycarbonylamino)-3'-methoxy-3'-phenylpropanoylamino)piperidine-1-carboxamidine (2'SR,3'RS)-N,N'-Di(benzyloxycarbonyl)-4-(2'-(tert-butyloxycarbonylamino)-3'-hydroxy-3'-phenylpropanoylamino)piperidine-1-carboxamidine (180 mg, 0.27 mmol), was dissolved in $CH_2Cl_2$ (30 ml). Iodomethane (190 mg, 1.3 mmol) and silver oxide (132 mg, 0.8 mmol) were added. After 18 h at 60° C. the mixture was filtered and the filtrate was evaporated in vacuo to give a brown oil which was purified by flash chromatography on silica gel (eluant: 50% ethyl acetate, 50% pet. ether) to give a white solid identified as (2'SR,3'RS)-N,N'-di(benzyloxycarbonyl)-4-(2'-(tert-butyloxycarbonylamino)-3'-methoxy-3'-phenylpropanoyl-amino)piperidine-1-carboxamidine (112 mg, 0.16 mmol, 61%).

6C. (2'SR,2"R, 3'RS)-N,N'-Di(benzyloxycarbonyl)-4-(2'-(2"-(tert-butyloxycarbonylamino)-3"-(4'"-ethoxyphenyl)propanoylamino)-3'-methoxy-3'-phenylpropanoylamino)piperidine-1-carboxamidine (2'SR,3'RS)-N,N'-Di(benzyloxycarbonyl)-4-(2'-(tert-butyloxycarbonylamino)-3'-methoxy-3'-phenylpropanoylamino)piperidine-1-carboxamidine (112 mg, 0.16 mmol) was dissolved in 4M HCl/dioxan (20 ml). After 30 min at room temperature the solvent was evaporated in vacuo and the residue dissolved in $CH_2Cl_2$ (30 ml). This solution was cooled to 0° C. and Boc-DTyr(Et)-OH (50 mg, 0.16 mmol) was added followed by PyBrop (76 mg, 0.16 mmol). The pH adjusted to 9 with N,N-diisopropylethylamine. The mixture was stirred at room temperature for 18 h, after which time the solvent was evaporated in vacuo and the residue dissolved in ethyl acetate (70 ml). This solution was washed with 0.3M $KHSO_4$ (1×20 ml), sat. $NaHCO_3$ (1×20 ml), water (1×20 ml) and brine (1×20 ml), dried ($Na_2SO_4$) and evaporated in vacuo to give a white solid which was purified by flash chromatography on silica gel (eluant: 65% chloroform, 15% hexane) to give a white solid identified as (2'SR,2"R, 3'RS)-N,N'-di(benzyloxycarbonyl)-4-(2'-(2"-(tert-butyloxycarbonylamino)-3"-(4'''-ethoxyphenyl)propanoylamino)-3'-methoxy-3'-phenylpropanoylamino)piperidine-1-carboxamidine (108 mg, 0.12 mmol, 75%).

6D. (2'S,2"R,3'R)-4-(2'-(2"-Amino-3"-(4'''-ethoxyphenyl)propanoylamino)-3'-methoxy-3'-phenylpropanoylamino)piperidine-1-carboxamidine trifluoroacetate (2'SR,2"R, 3'RS)-N,N-Di(benzyloxycarbonyl)-4-(2'-(2"-(tert-butyloxycarbonylamino)-3"-(4'''-ethoxyphenyl)propanoylamino)-3'-methoxy-3'-phenylpropanoylamino)piperidine-1-carboxamidine (108 mg, 0.12 mmol) was dissolved in 4M HCl/dioxan (20 ml). After 30 min at room temperature the solvent was evaporated in vacuo and the residue dissolved in AcOH/water (95:5, 20 ml). This solution was hydrogenated over 10% palladium on charcoal. After 2 h at room temperature the mixture was filtered through Celite and the residue washed with AcOH/water (9:1, 30 ml). The combined filtrates were evaporated in vacuo and the residue purified by mplc on Vydac $C_{18}$ (15-25μ) using MeCN/H$_2$O/TFA to give a white solid identified as (2'S,2"R,3'R)-4-(2'-(2"-amino-3"-(4'''-ethoxyphenyl)-propanoylamino)-3'-methoxy-3'-phenylpropanoylamino)piperidine-1-carboxamidine trifluoroacetate (18 mg).

[M+H]$^+$=511.3

The following compounds were prepared using analogous methods.

Examples 7-17

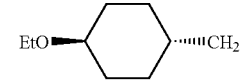

| Ex. | R$^1$ | R$^2$ | m/e |
|---|---|---|---|
| 7 | H | (CH$_3$)$_2$CHCH$_2$ | 403.3 |
| 8 | H | c-C$_6$H$_{11}$ | 429.3 |
| 9 | H | c-C$_8$H$_{11}$CH$_2$ | 443.4 |
| 10 | H | c-C$_6$H$_{11}$CH$_2$CH$_2$ | 457.4 |
| 11 | H | (trans EtO-cyclohexyl-CH$_2$) | 487.4 |
| 12 | H | (cis/trans EtO-cyclohexyl-CH$_2$) | 487.4 |
| 13 | H | (decahydronaphthyl-CH$_2$) | 497.4 |
| 14 | HO$_2$CCH$_2$ | | 555 |
| 15 | MeO$_2$CCH$_2$ | | 569 |

Examples 18-52

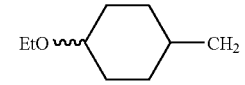

| Ex. | R$^1$ | R$^2$ | m/e |
|---|---|---|---|
| 16 | H | PhCH$_2$CH$_2$ | 451.2 |
| 17 | H | PhCH$_2$OCH$_2$ | 467.2 |

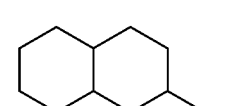

| Ex. | R$^1$ | S$^1$ | S$^2$ | S$^3$ | S$^4$ | m/e |
|---|---|---|---|---|---|---|
| 18 | H | H | H | H | H | 437.3 |
| 19 | H | H | H | CH$_3$CH$_2$CH$_2$ | H | 479 |
| 20 | H | H | H | NO$_2$ | H | 482.3 |
| 21 | H | H | H | NH$_2$ | H | 452.3 |
| 22 | H | H | H | I | H | 563.1 |
| 23 | H | H | H | F | H | 455.2 |
| 24 | H | H | H | CN | H | 462.3 |
| 25 | H | H | H | Cl | H | 471.6 |
| 26 | H | H | H | CF$_3$ | H | 505.3 |
| 27 | H | H | H | NHCOCH$_3$ | H | 494.3 |
| 28 | H | H | F | H | H | 455 |
| 29 | H | H | Cl | Cl | H | 505.1 |
| 30 | H | H | Cl | Cl | H | 505.1 |
| 31 | H | H | H | OH | H | 453.3 |
| 32 | H | H | H | OCH$_2$Ph | H | 543.5 |
| 33 | H | H | H | OC(CH$_3$)$_3$ | H | 509.3 |
| 34 | H | H | H | OCH$_2$CH$_2$CH$_3$ | H | 495.4 |
| 35 | H | H | H | OCH$_3$ | H | 467.3 |
| 36 | H | H | H | OCH(CH$_3$)$_2$ | H | 495.2 |
| 37 | H | H | H | OnC$_6$H$_{13}$ | H | 537.3 |
| 38 | H | H | I | OCH$_2$CH$_3$ | I | 733.1 |
| 39 | CH$_3$ | H | H | OCH$_2$CH$_3$ | H | 493.3 |
| 40 | CH$_3$SO$_2$ | H | H | OCH$_2$CH$_3$ | H | 559.3 |
| 41 | CH$_3$CH$_2$SO$_2$ | H | H | OCH$_2$CH$_3$ | H | 573.3 |
| 42 | PhSO$_2$ | H | H | OCH$_2$CH$_3$ | H | 621 |
| 43 | CH$_3$CO | H | H | OCH$_2$CH$_3$ | H | 523.3 |
| 44 | CH$_3$CH$_2$CH$_2$CO | H | H | OCH$_2$CH$_3$ | H | 551 |
| 45 | CH$_3$CO | H | H | OCH$_2$CH$_3$ | H | 537 |
| 46 | PhCH$_2$OCO | H | H | OCH$_2$CH$_3$ | H | 615 |
| 47 | MeO$_2$CCH$_2$ | H | H | OCH$_2$CH$_3$ | H | 553 |
| 48 | HO$_2$CCH$_2$ | H | H | OCH$_2$CH$_3$ | H | 539 |
| 49 | H | —CH=CH—CH=CH— | | | H | 487.4 |
| 50 | H | H | —CH=CH—CH=CH— | | H | 487.3 |

-continued

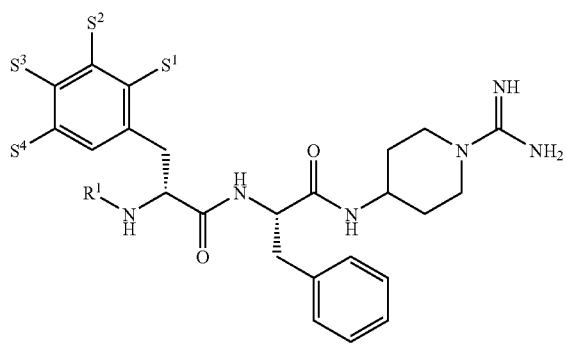

| Ex. | R$^1$ | S$^1$ | S$^2$ | S$^3$ | S$^4$ | m/e |
|-----|-------|-------|-------|-------|-------|-------|
| 51 | —CH$_2$— | H | H | H | H | 449.3 |
| 52 | —CH$_2$— | H | H | OCH$_2$CH$_3$ | H | 493.3 |

Examples 53-54

| Ex. | R$^3$ | m/e |
|-----|-------|-----|
| 53 | OH | 497.4 |
| 54 | OMe | 511.3 |

Examples 55-58

| Ex. | S$^1$ | S$^2$ | m/e |
|-----|-------|-------|-----|
| 55 | H | OH | 453.3 |
| 56 | H | OMe | 467.3 |
| 57 | OH | H | 453.3 |
| 58 | OMe | H | 467.3 |

Example 59

Determination of the Inhibition Constant $K_i$ for Plasma Kallikrein

Inhibition of plasma kallikrein activity in vitro was determined using standard published methods (see e.g. Johansen et al., Int. J. Tiss. Reac. 1986, 8, 185; Shori et al., Biochem. Pharmacol., 1992, 43, 1209; Stüjrzebecher et al., Biol. Chem. Hoppe-Seyler, 1992, 373, 1025). Human plasma kallikrein (Callbiochem) was incubated at 37° C. with three different concentrations of the chromogenic substrate S-2302 (Chromogenix AB) and various concentrations of the test compound. Residual enzyme activity (initial rate of reaction) was determined by measuring the change in optical absorbance at 405 nm and the inhibitory constant $K_i$ for the test compound as determined from a Dixon plot (Dixon, Biochem. J., 1953, 55, 170). Typical results are presented in the Table.

| Compound of Example No | $K_i$ (nM) |
|------------------------|------------|
| 1  | 4.5 |
| 2  | 66.0 |
| 3  | 3.0 |
| 4  | 1.4 |
| 5  | 6.6 |
| 6  | 25.0 |
| 14 | 2.6 |
| 15 | 19.0 |
| 32 | 5.5 |
| 34 | 7.0 |
| 39 | 15.0 |
| 40 | 9.0 |
| 42 | 4.5 |
| 43 | 7.3 |
| 44 | 4.1 |
| 45 | 3.0 |
| 52 | 18.0 |

Example 60

Determination of Enzyme Selectivity

Selected compounds were further screened for inhibitory activity against other trypsin-like proteases following the method of Example 59 and using the appropriate enzyme and chromogenic substrate (Chromogenix AB). Representative results are presented in the Table. The selectivity is given by:

Selectivity=($K_i$ for test enzyme)/($K_i$ for plasma kallikrein)

| Enzyme | Substrate | Compound of Example No | $K_i$ (nM) | Selectivity |
|--------|-----------|------------------------|------------|-------------|
| Human Tissue Kallikrein | S-2266 | 1 | 45,000 | 10,000 |
| | | 3 | 6,000 | 2,000 |
| | | 4 | 18,500 | 13,000 |
| | | 5 | >70,000 | >10,000 |
| | | 39 | 14,000 | 930 |
| | | 40 | 1,950 | 210 |
| | | 42 | 6,800 | 1,500 |
| | | 43 | 69,000 | 9,400 |
| | | 45 | 49,000 | 16,000 |
| Thrombin | S-2238 | 3 | 310 | 100 |
| | | 40 | 16,500 | 1,800 |
| Plasmin | S-2390 | 3 | 3,200 | 1,000 |
| | | 40 | 1,440 | 160 |

-continued

| Enzyme | Substrate | Compound of Example No | $K_i$ (nM) | Selectivity |
|---|---|---|---|---|
| Trypsin | S-2222 | 3 | 825 | 270 |
| | | 40 | 3,500 | 380 |

The invention claimed is:

1. A compound according to general formula 1, or a pharmaceutically acceptable salt thereof,

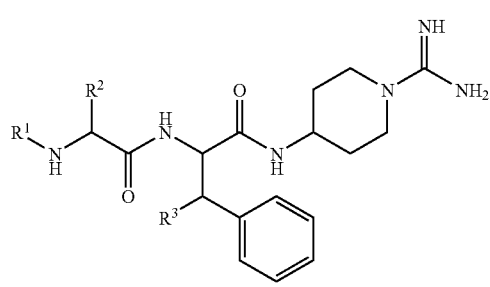

wherein
R$^1$ is selected from H, lower alkyl, R$^4$—CO, R$^4$—O$_2$CCH$_2$, R$^5$—OCO and R$^5$—SO$_2$;
R$^2$ is selected from (C$_6$-C$_{10}$)cycloalkylmethyl, benzyl optionally substituted with up to three groups chosen from F, Cl, Br, OH, lower alkyl and O-(lower alkyl), phenethyl optionally substituted with up to three groups chosen from F, Cl, Br, OH, lower alkyl and O-(lower alkyl) and benzyloxymethyl optionally substituted with up to three groups chosen from F, Cl, Br, OH, lower alkyl and O-(lower alkyl);
R$^3$ is selected from H, OH and O-lower alkyl;
R$^4$ is selected from H, lower alkyl and phenyl; and
R$^5$ is selected from lower alkyl, phenyl and benzyl.

2. A compound according to claim 1 wherein R$^1$ is selected from H, lower alkyl, and R$^4$—O$_2$CCH$_2$.

3. A compound according to claim 1 wherein R$^2$ is selected from cyclohexylmethyl, decahydronaphth-2-ylmethyl, benzyl, 4-fluorobenzyl, 4-chlorobenzyl, 4-hydroxybenzyl, 4-(lower alkyl)oxybenzyl, α-hydroxybenzyl, α-methoxybenzyl, phenethyl and benzyloxymethyl.

4. A compound according to claim 1 wherein the absolute stereochemistry is as depicted in general formula 1A.

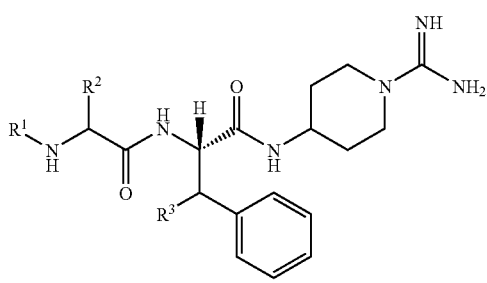

5. A compound according to claim 1 wherein the absolute stereochemistry is as depicted in general formula 1B.

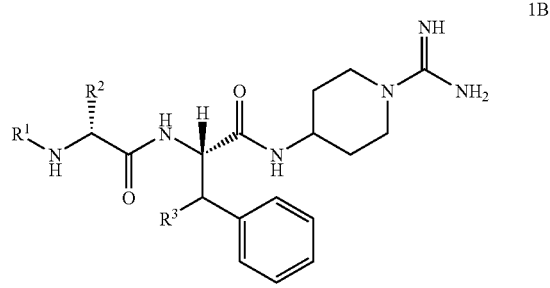

6. A compound according to claim 1 selected from
(2'S,2"R)-4-(2'-(2"-amino-3"-(4'''-ethoxyphenyl)propanoylamino)-3'-phenylpropanoyl-amino)piperidine-1-carboxamidine;
(2'S,2"R)-4-(2'-(2"-carboxymethylamino-3"-(4'''-ethoxyphenyl)propanoylamino)-3-phenylpropanoylamino)piperidine-1-carboxamidine;
(2'S,2"R)-4-(2'-(3"-(4'''-ethoxyphenyl)-2"-(methyloxycarbonylmethylamino)-propa- noylamino)-3'-phenylpropanoylamino)piperidine-1-carboxamidine;
(2'S,2"R)-4-(2'-(2"-amino-3"-cyclohexylpropanoylamino)-3'-phenylpropan-oylamino)piperidine- 1-carboxamidine;
(2'S,2"R)-4-(2'-(2"-carboxymethylamino-3"-cyclohexylpropanoylamino)-3-phenylpropanoylamino)piperidine- 1-carboxamidine;
(2'S,2"R)-4-(2'-(3"-cyclohexyl-2"-(methyloxycarbonylmethylamino)propanoylamino)-3-phenylpropanoylamino)piperidine-1-carboxamidine;
(2'S,2"R)-4-(2'-(2"-amino-3"-phenylpropanoylamino)-3-phenylpropanoylamino)piperidine-1-carboxamidine;
(2'S,2"R)-4-(2'-(2"-carboxymethylamino-3"-phenylpropanoylamino)-3 '-phenyl-propanoylamino)piperidine-1-carboxamidine;
(2'S,2"R)-4-(2'-(2"-(methyloxycarbonylmethylamino)-3"-phenylpropanoylamino)-3-phenylpropanoylamino)piperidine-1-carboxamidine;
(2'S,2"R)-4-(2'-(2"-amino-3"-decahydronaphth-2'''-ylpropanoylamino)-3'-phenylpropanoylamino)piperidine-1-carboxamidine;
(2'S,2"R)-4-(2'-(2"-carboxymethylamino-3"-decahydronaphth-2'''-ylpropanoylamino)-3'-phenylpropanoylamino)piperidine- 1 -carboxamidine;
(2'S,2"R)-4-(2'-(3"-decahydronaphth-2'''-yl-2"-(methyloxycarbonylmethylamino) propanoylamino)-3'-phenylpropanoylamino)piperidine-1-carboxamidine;
(2'S,2"R,3'R)-4-(2'-(2"-amino-3"-cyclohexylpropanoylamino)-3'-hydroxy--3'-phenylpropanoylamino)piperidine-1 -carboxamidine;
(2'S,2"R,3'R)-4-(2'-(2"-carboxymethylamino-3"-cyclohexylpropanoylamino)-3'-hydroxy-3'phenylpropanoylamino)piperidine-1-carboxamidine;
(2'S,2"R,3'R)-4-(2'-(3"-cyclohexyl-2"-(methyloxycarbonylmethylamino)propanoylamino)-3-hydroxy-3'-phenylpropanoylamino)piperidine-1-carboxamidine;

(2'S,2"R,3'R)-4-(2'-(2"-amino-3"-(4'"-ethoxyphenyl)propanoylamino)-3'-methoxy-3'-phenylpropanoylamino)piperidine-1-carboxamidine;

(2-S,2"R,3'R)-4-(2'-(2"-carboxymethylamino-3"-(4'"-ethoxyphenyl)propanoylamino)-3'-methoxy-3'-phenylpropanoylamino)piperidine-1-carboxamidine; and (2'S,2"R,3'R)-4-(2'-(3"-(4'"-ethoxyphenyl)-2"-(methyloxycarbonylmethy-lamino)propanoylamino)-3'-methoxy-3'-phenylpropanoylamino)piperidine-1-carboxamidine or a pharmaceutically acceptable salt thereof.

* * * * *

UNITED STATES PATENT AND TRADEMARK OFFICE
CERTIFICATE OF CORRECTION

PATENT NO. : 7,649,000 B2  Page 1 of 1
APPLICATION NO. : 10/506535
DATED : January 19, 2010
INVENTOR(S) : David Michael Evans It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 952 days.

Signed and Sealed this

Twenty-third Day of November, 2010

David J. Kappos
*Director of the United States Patent and Trademark Office*